(12) United States Patent
Manasas et al.

(10) Patent No.: US 6,371,991 B1
(45) Date of Patent: *Apr. 16, 2002

(54) ALIGNMENT GUIDE FOR FLUTED PROSTHETIC STEMS

(75) Inventors: Mark Allan Manasas, Easton, MA (US); Alfred F. DeCarlo, Jr., Stamford, CT (US); Michael S. Varieur, Attleboro, MA (US)

(73) Assignee: Depuy Orthopaedics, Inc., Warsaw, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/102,721

(22) Filed: Jun. 22, 1998

Related U.S. Application Data

(63) Continuation-in-part of application No. 08/772,630, filed on Dec. 23, 1996, now abandoned.

(51) Int. Cl.⁷ ............................ A61F 2/32; A61B 17/90
(52) U.S. Cl. .............................. 623/22.12; 623/22.35; 623/23.44; 606/95; 606/99
(58) Field of Search .............................. 606/86, 87, 95, 606/98, 99, 102, 104; 623/18, 23, 22, 18.11, 22.12, 23.35, 23.44, 23.11

(56) References Cited

U.S. PATENT DOCUMENTS

| | | | |
|---|---|---|---|
| 4,790,852 A | 12/1988 | Noiles | 623/18 |
| 4,827,919 A | 5/1989 | Barbarito et al. | 128/92 |
| 4,997,448 A | 3/1991 | Filer | 623/23 |
| 5,171,324 A * | 12/1992 | Campana et al. | 623/23 |
| 5,342,366 A | 8/1994 | Whiteside et al. | 606/86 |
| 5,387,216 A | 2/1995 | Thornhill et al. | 606/88 |
| 5,409,492 A * | 4/1995 | Jones et al. | 606/86 |
| 5,464,406 A | 11/1995 | Ritter et al. | 606/86 |
| 5,480,452 A | 1/1996 | Hofmann et al. | 623/23 |
| 5,514,136 A * | 5/1996 | Richelsoph | 606/99 |
| 5,601,567 A | 2/1997 | Swajger et al. | 606/102 |
| 5,674,225 A | 10/1997 | Muller | 606/99 |
| 5,755,793 A | 5/1998 | Smith et al. | 623/16 |
| 5,766,262 A | 6/1998 | Mikhail | 623/23 |
| 5,888,208 A * | 3/1999 | Ro | 623/23 |
| 5,888,245 A * | 3/1999 | Meulink et al. | 606/99 |

FOREIGN PATENT DOCUMENTS

| | | | |
|---|---|---|---|
| EP | 0342014 | 11/1989 | A61F/2/36 |
| EP | 0850610 | 7/1998 | A61F/2/46 |
| FR | 2660854 | 10/1991 | A61F/2/32 |
| WO | WO88/01854 | 3/1988 | A61F/2/30 |

* cited by examiner

Primary Examiner—Bruce Snow (57) ABSTRACT

An alignable orthopedic prosthesis system includes a prosthesis and an alignment guide. The prosthesis includes a stem having at least one keyed component extending along its outer surface. The alignment guide has an alignment body with a guide surface disposed on an inner portion thereof. The guide surface has a key element formed therein for engageably receiving the keyed component of the prosthesis.

14 Claims, 8 Drawing Sheets

ALIGNMENT GUIDE FOR FLUTED PROSTHETIC STEMS

CROSS-REFERENCE TO RELATED APPLICATIONS

This application is a continuation-in-part of U.S. patent application Ser. No. 08/772,630, filed Dec. 23, 1996, now abandoned.

STATEMENT REGARDING FEDERALLY SPONSORED RESEARCH

Not Applicable.

FIELD OF THE INVENTION

The present invention relates to an alignment guide for ensuring proper alignment or orientation of a prosthetic stem in bone.

BACKGROUND OF THE INVENTION

Stems are used in prosthetic joint implants to anchor the implant in a bone cavity. The bone for receiving the stem is typically prepared by drilling a hole in the bone and creating an opening sized and contoured to receive the stem of the implant. The stem is inserted into a prepared cavity of a bone and a joint bearing surface attached or coupled to the stem, extends out to the cavity. Many stems are fluted, i.e., they have distally extending longitudinal grooves in the stems that provide greater stability and anchoring of the stem once it is inserted into the prepared cavity.

Typically, once a fluted stem is inserted into a prepared cavity, it is extremely difficult to rotate the stem to properly reorient it. In order to do so the stem must be removed and reinserted which can damage bone and increase operative time. Typically, the stem is aligned by marking the bone and the stem and using the marks to align the stem with respect to the bone. The drawback to this method is the potential imprecision in the alignment. Because the landmark on the stem and bone are not in close proximity to each other, parallax and other problems associated with alignment by eye may result. Also, the stem may move from its aligned position as it is inserted.

Accordingly, it is an object of the present invention to provide a means for aligning a fluted stem of an orthopedic implant prior to and as it is being inserted into a prepared bone cavity.

SUMMARY OF THE INVENTION

The present invention provides a method and device for inserting a keyed or fluted prosthetic component in an aligned position into a prepared bone cavity. The bone is prepared by removing bone material from the bone canal and by machining an opening of a predetermined shape in the bone cavity. An alignment guide having an outer shape conforming with that of the machined opening is inserted into the bone cavity. The alignment guide also has an inner shape or key element corresponding to the outer shape of the fluted stem of the implant that engages the stem, preferably in a manner which provides contact with a small area of the stem. In a preferred embodiment the inner shape of the alignment guide includes notches or grooves for receiving the flutes of the stem. Another aspect of a preferred embodiment may provide protrusions in the alignment guide that make contact with certain keyed elements of the prosthesis to be inserted.

In a preferred embodiment, the alignment guide is formed generally in a broken circle or circumference to allow flexibility in removing the alignment guide. The alignment guide further comprises a means for lifting the alignment guide from the bone cavity once the stem is inserted through the alignment guide. This means may, for example, be a tab or protrusion or an opening for inserting a tool to pry out the guide. In a further embodiment, the alignment guide includes a guide body that is disposed at the distal end of a handle.

In a preferred embodiment, once the bone cavity is prepared and the alignment guide is inserted, a fluted stem of a prosthetic implant is positioned or oriented with respect to the stem axis and is then inserted into the alignment guide with the flutes extending into the notches of the alignment guide. Once the stem is inserted in the guide, the position or orientation is held true until the stem is seated into the bone cavity. As the stem is inserted, the flutes form a path within the bone cavity that the stem will generally follow during the insertion of the final segment of the stem. Once this has occurred the alignment guide may be removed by pulling the tab. The insertion is completed by extending the implant all the way into the opening until the proximal geometry of the stem is placed within the machined opening in the bone. This stem proximal geometry is also of a shape that corresponds to the machined opening so that the implant fits within the bone cavity.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

The following is a description of a preferred embodiment of the present invention in use with a hip stem implant. Referring now to FIGS. 1 through 4, an alignment guide 10 is illustrated. The alignment guide 10 comprises a body 11, a guide portion 12, and an opening 14. The body 11 and guide portion 12 form an outer shape that corresponds to at least a portion of a machined cavity 21 in the bone 20. The guide portion 12 has an inner circumference 15 having grooves or notches 16 for receiving flutes 31 of the stem 30 an implant 50. Protrusions 13 in the guide portion 12 may contact the stem 30 of the implant 50. In this embodiment, the grooves 16 and the protrusions 13 form a key for guiding insertion of the stem 30 into the bone cavity. In variations of this embodiment grooves 16, protrusions 13 or the like may be used alone or together to key insertion of the keyed stem 30.

Figure 1:
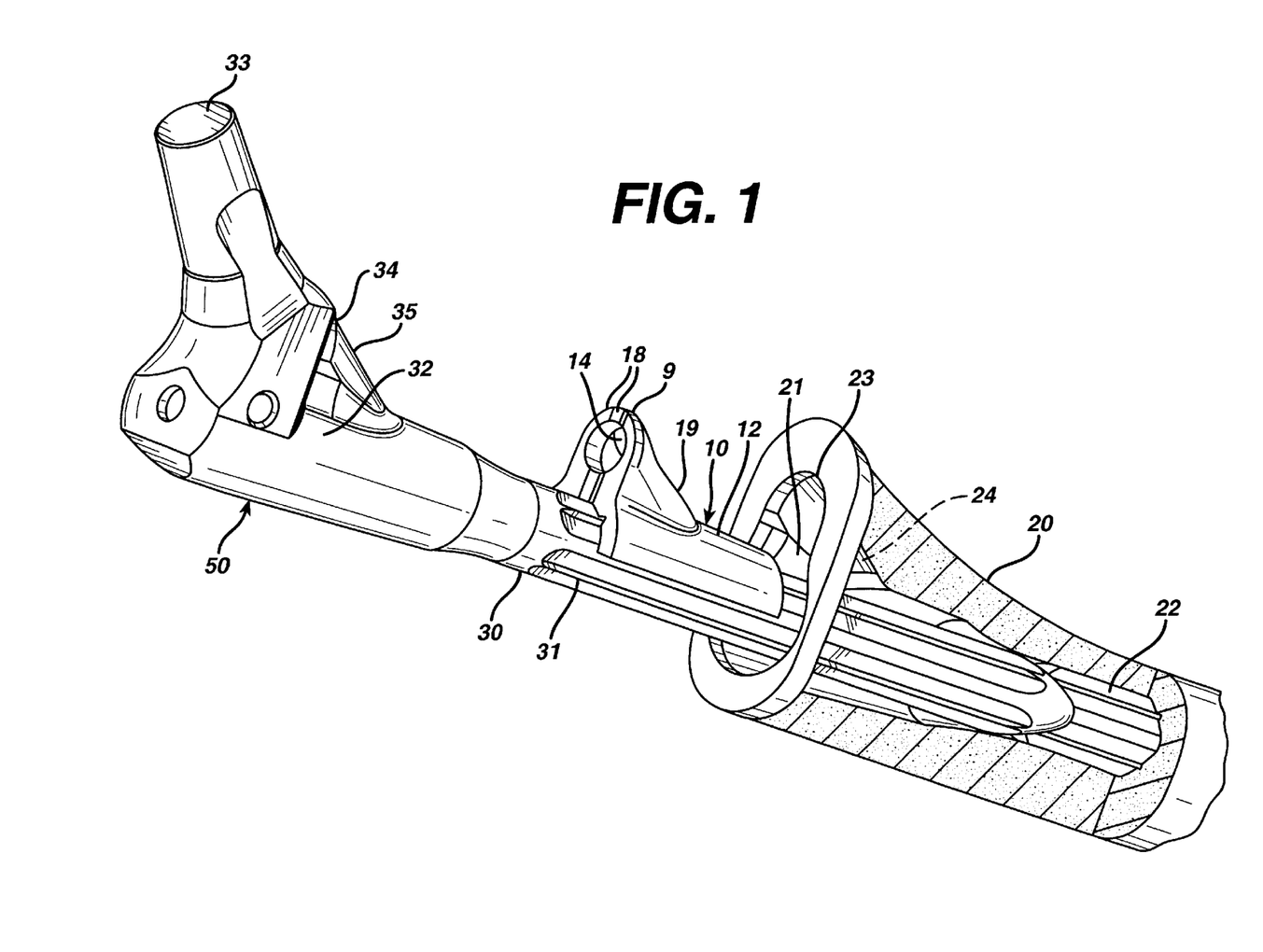
FIG. 1 illustrates an exploded perspective view of a bone with a partial break away of a prepared cavity, an alignment guide and an implant inserted through the alignment guide.

FIG. 1 illustrates a prepared bone 20 having a machined cavity 21 and a longitudinal cavity 22 formed in the canal of the bone. At least a portion of the machined cavity 21 has a shape corresponding to the shape of the alignment guide 10. FIG. 1 further illustrates an implant 50 comprising a stem 30 having flutes 31 distally extending along the length of the stem 30; a protrusion or proximal geometry 35 shaped to fit within the machined cavity 21 of the bone; and a neck 33 extending from the proximal end of the implant for receiving a ball portion of a ball and socket joint.

The notches 16 in the inner circumference 15 of the guide are placed so that when the stem 30 is inserted into the alignment guide 10, the flutes 31 of the stem 30 fit within the notches 16 in the alignment guide 10 to hold or guide the stem 30 in an appropriate or aligned position within the bone cavity.

In this embodiment the shape of the machined bone cavity 21 is generally tapered to form an elliptical end portion 23. The alignment guide 10 is similarly shaped with the body 11 forming an elliptical end portion 18 on the proximal end of the body. The implant 50 as well includes a similarly shaped proximal section with an elliptical end portion 34. The bone cavity 21, further comprises a cut 24 corresponding to tapers 19, 35 on the alignment guide 10 and the implant 50 respectively. The cut 24 of the bone cavity 21 and the taper 19 of the alignment guide 10 prevent the alignment guide 10 from being inserted too far into the bone cavities 21, 22. The cut 24 of the bone cavity 21 and the taper 35 of the implant 50 similarly prevent the implant 50 from being inserted too far into the bone cavities, 21, 22 and thus prevent the neck 33 from being in an improper position.

Figure 2:
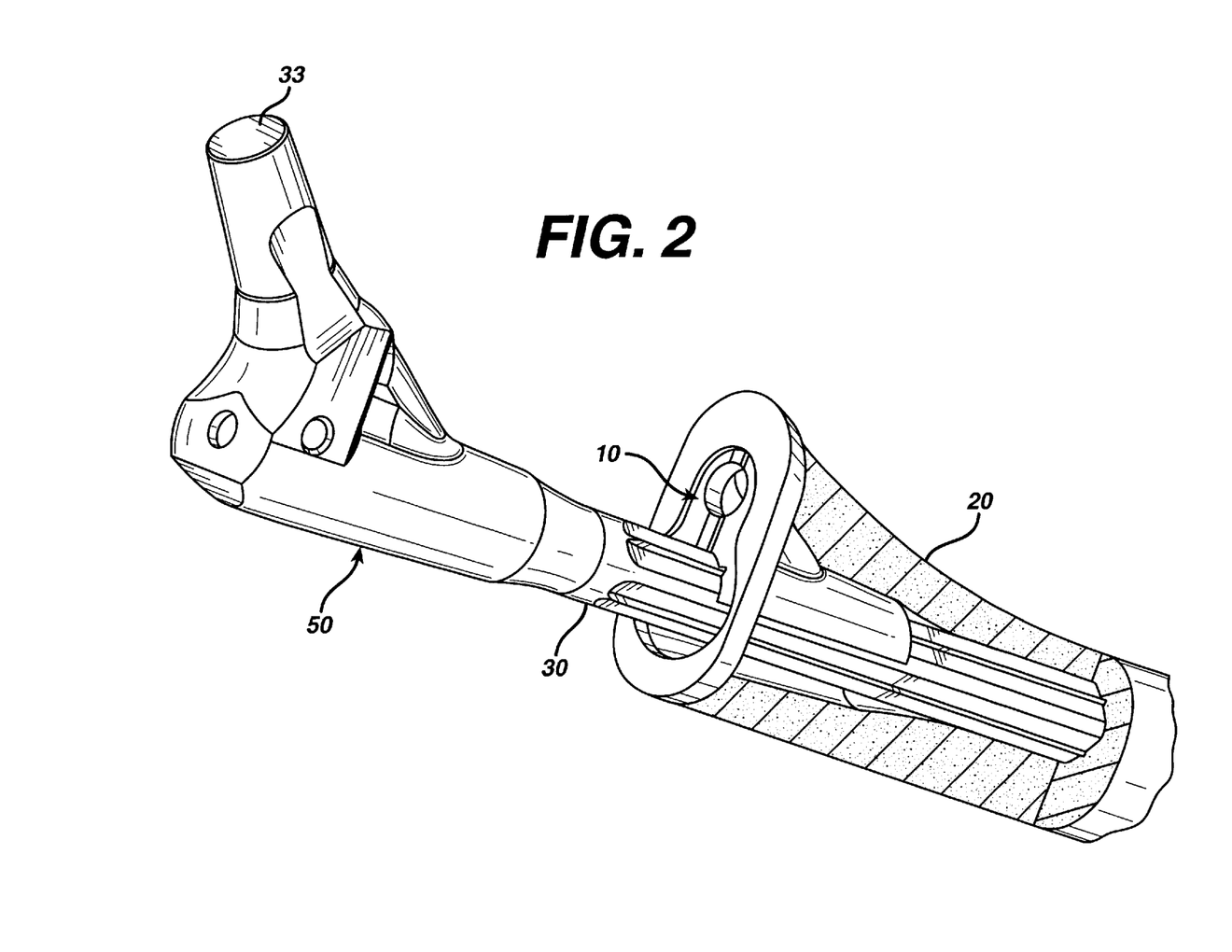
FIG. 2 illustrates a perspective view of the bone, alignment guide and implant of FIG. 1 with the alignment guide in place and the implant inserted partially into the bone through the alignment guide.
Figure 3:
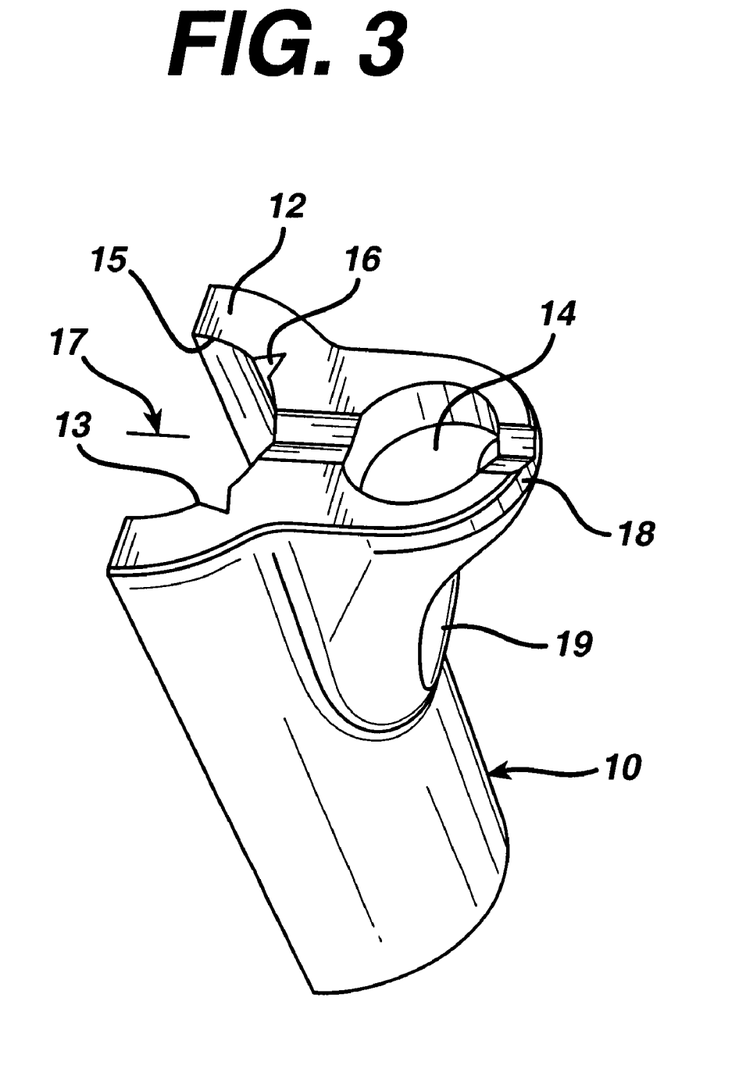
FIG. 3 illustrates a perspective view of the alignment guide of the present invention.

In use, the alignment guide 10 is inserted into the machined bone cavity 21 with the elliptical end portion 18 of the alignment guide 10 in alignment with the elliptical end portion 23 of the machined cavity 21. The stem 30 of the implant 50 is placed in the inner circumference 15 of the guide portion 12 of the alignment guide 10 with the elliptical end portion 34 of the implant 50 generally in line with a groove 9 across the elliptical end portion 18 of the alignment guide 10. In order to insert the implant 50 properly aligned, the proximal geometry 32 is generally aligned so that it will fit within the machined bone cavity 21. The flutes 31 are placed within the notches 16 of the guide portion 12 and the implant 50 is driven into the bone cavity 22 guided by the alignment guide 10. When the implant 50 is generally in the bone cavities 21, 22 but prior to complete insertion, as illustrated in FIG. 2, the alignment guide 10 is removed by inserting a device into the opening 14 in the guide 10 to remove it from the bone cavity 21 and from the stem 30 of the implant 50. The implant 50 is then further driven into place with the elliptical end portion 34 fitting within the elliptical end portion 23 of the bone and the taper 35 abutting adjacent a cut 24 of the bone cavity 21.

Figure 4:
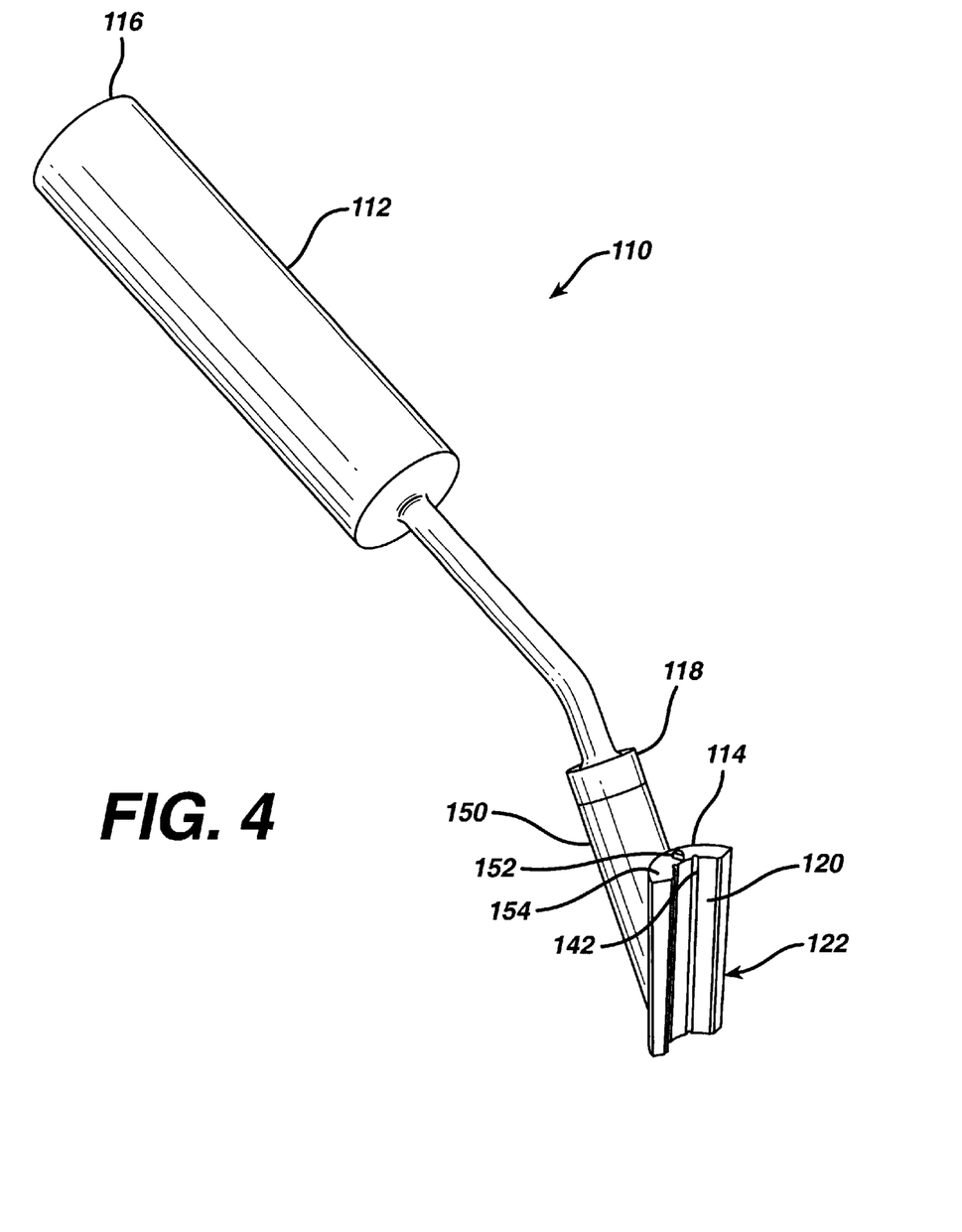
FIG. 4 is a perspective view of an alignment guide of the invention.
Figure 5:
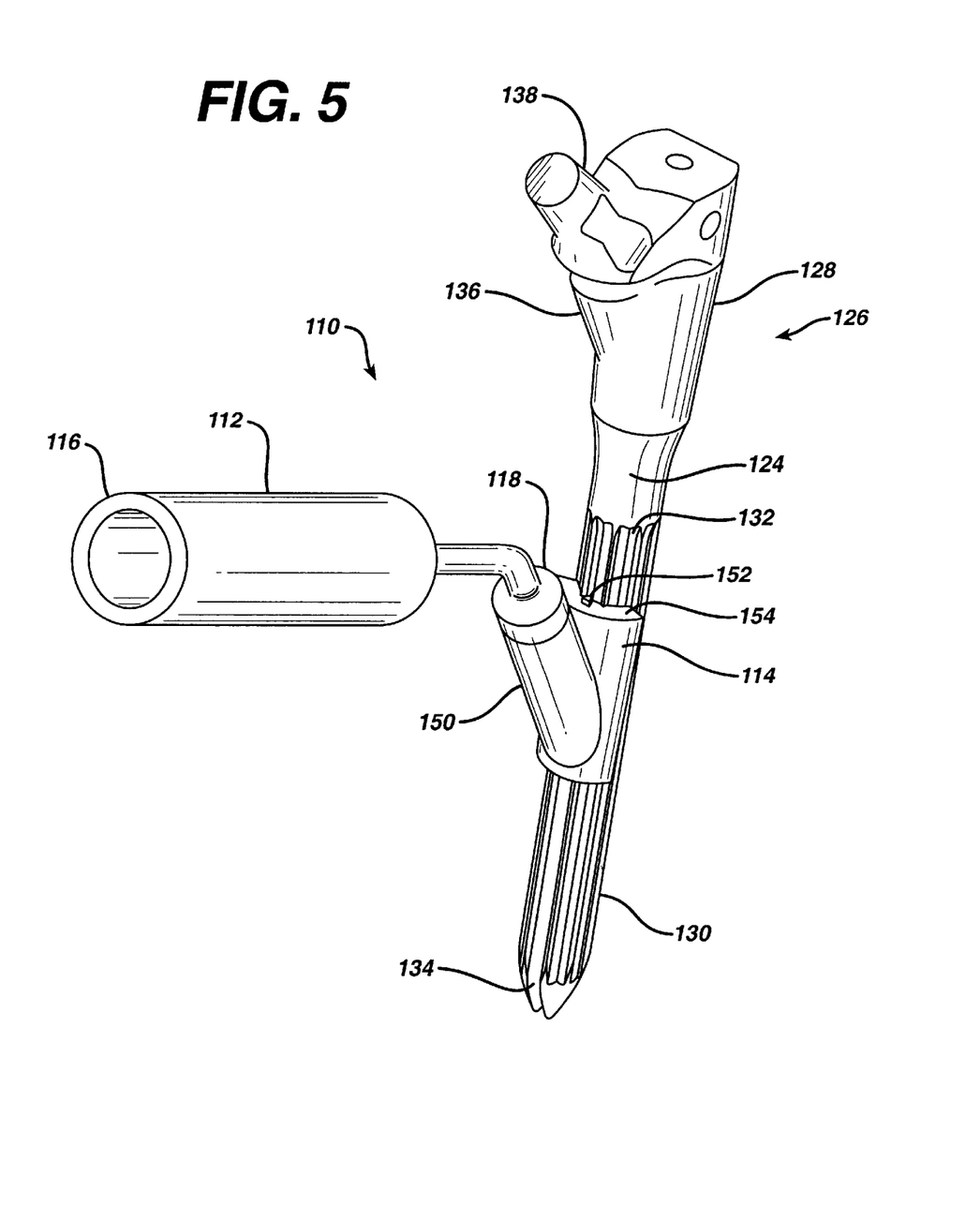
FIG. 5 is a perspective view of the alignment guide of FIG. 4 in contact with a fluted stem of a hip prosthesis femoral component.

An additional alignment guide 110 of the invention, illustrated in FIG. 4, has a handle 112 and an alignment body 114. The handle 112 is generally shaped so as to be easily grasped by a surgeon and has proximal and distal ends 116, 118. The alignment body 114 is located at the distal end 118 of the handle 112 and has a guide surface 120 disposed on an inner portion 122 thereof. The guide surface 120 is releasably engageable with an outer surface 124 of a prosthetic stem 126 as shown in FIG. 5.

The illustrated stem 126 is adapted for use as the femoral component of a hip prosthesis, however, the system of the invention is useful with a variety of prosthetic implants, especially those suited for implantation in a long bone. The prosthetic stem 126 may have proximal and distal portions 128, 130 and have at least one flute 132 formed on its outer surface 124. The distal portion 128 of the stem 126 is substantially cylindrical and may also include a slot 134, in particular, a coronal slot. The proximal portion 128 of the stem may have an angled region 136 or proximal spout having an elliptical cross-section leading to a neck 138. The preparation of a bone cavity (such as bone cavity 21 of FIG. 1) adapted to such a geometry is illustrated in U.S. Pat. No. 4,790,852 to Noiles which is hereby incorporated by reference. A person of ordinary skill in the art will recognize that other reaming or broaching techniques may also be used to create a bone geometry corresponding to the illustrated stem 126.

For use in the present invention, stem 126 has at least one surface element or keyed component, such as flute 132, disposed on its outer surface 124 that is angled with respect to the outer surface 124 and extends in the direction of a longitudinal axis 140 (FIG. 6) of the stem 126. As illustrated in FIGS. 1–2 and 6–8, the stem surface elements may include a plurality of flutes. Generally, these angled surface features 132 may include any combination of indentations or protrusions from the outer surface 124 suitable to hold the stem 126 against rotational misalignment when engaged with the alignment guide 110.

Figure 6:
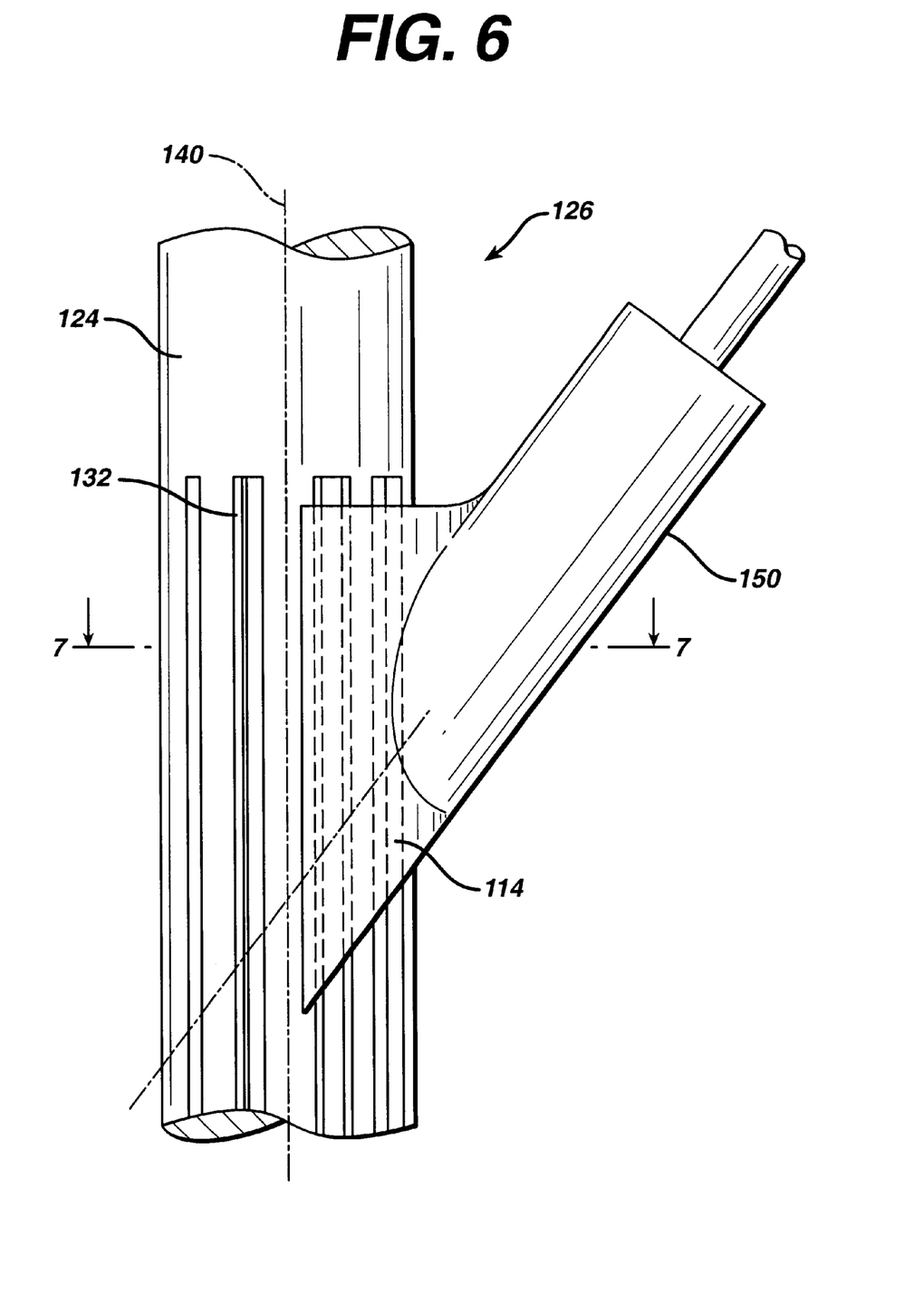
FIG. 6 is a side view of the alignment guide and fluted stem of FIG. 5.
Figure 7:
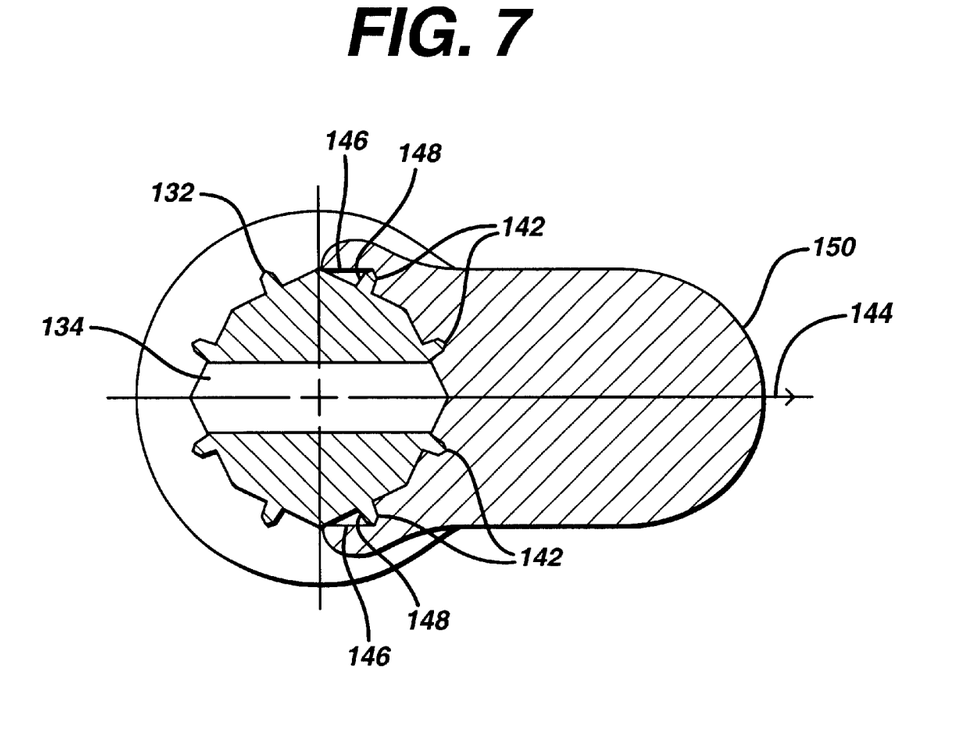
FIG. 7 is a cross sectional view of the alignment guide and fluted stem of FIG. 6 taken along line 7—7.

The guide surface 120 of the alignment guide 110 engages the outer surface 124 of the stem 126, as shown in FIGS. 6–7, around the cylindrical stem 126 generally up to about 180°. The guide surface 120 also includes one or more angled guide surface features 142 which form a key to engage the stem surface features 132 to hold the stem 126 against rotation. The angled guide surface features 142 are also formed so that the guide 110 may be removed from its engagement with the stem 126 in a plane transverse to the longitudinal axis 140 as illustrated by the lateral axis 144 and referred to herein as a lateral direction, which, in the illustrated embodiment, is directed from lateral to medial for a hip prosthesis embodiment.

In the illustrated embodiment, the outermost guide surface features 142 (FIG. 7) each have an outer angled surface 146 formed to allow lateral disengagement. That is, rather than contacting a stem surface feature 132, the outer angled surface 146 is generally in the direction of the lateral axis 144 so as not to engage a lateral facing surface 148 of the stem surface element 132, thus permitting lateral removal of the alignment guide 110 from the stem 126.

In the embodiment illustrated in FIGS. 4 to 8, the alignment guide 110 may have a tapered outer shape 150 to correspond to the shape of the bone cavity into which the stem 126 is being implanted. The alignment guide 110 may also have an alignment marker 152 located on a proximal surface 154 of the guide body 114 to provide a visual aid for engaging the stem 126 with the alignment guide 110.

Figure 8:
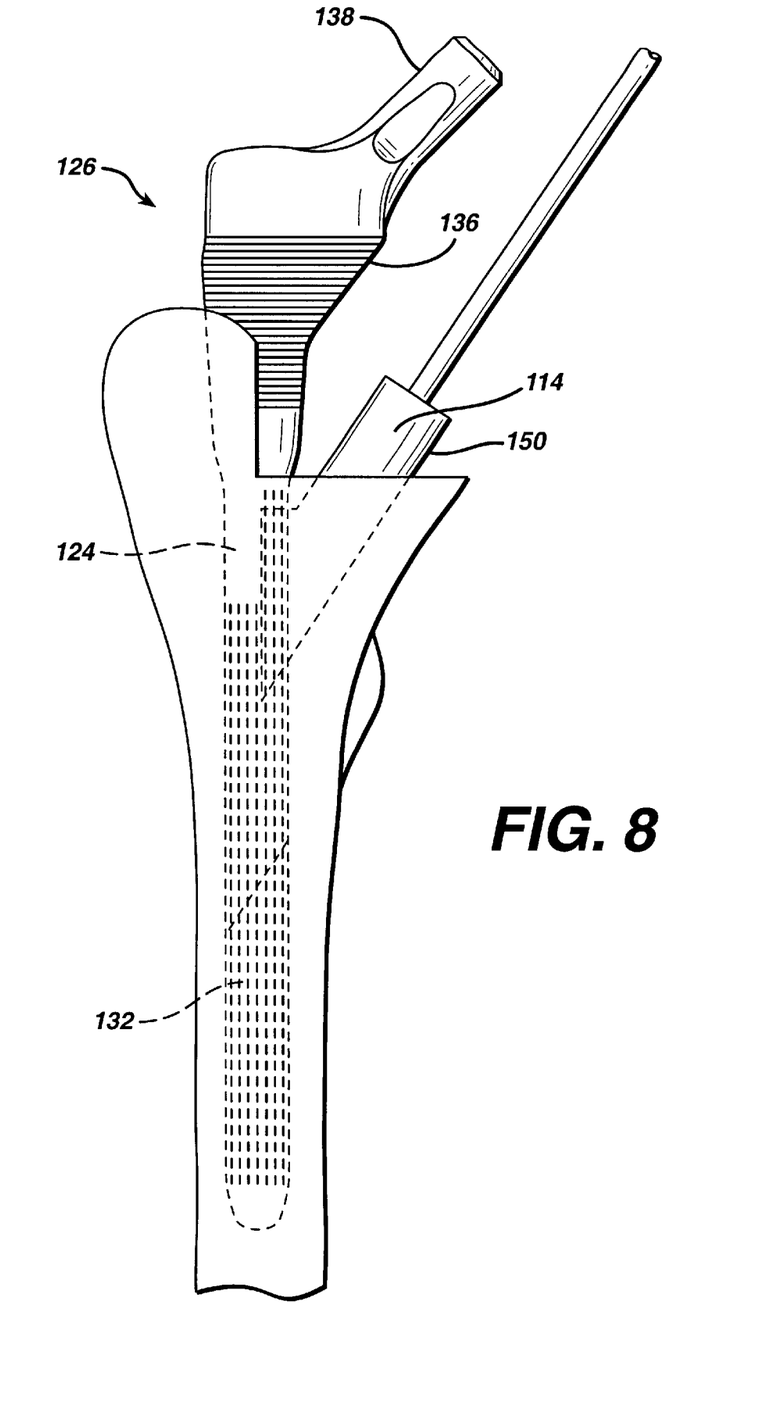
FIG. 8 is a side view of an alignment guide and prosthetic stem component of the invention being inserted into a bone.

A method for inserting a prosthetic stem 126 into a long bone begins with the preparation of a suitable cavity in the long bone. Where, as illustrated in FIG. 8, the stem 126 includes features such as a tapered proximal spout 150, the cavity should be formed so as to correspond to such features.

The prosthetic stem 126 is placed at the opening of the cavity in the long bone in a predetermined rotational orientation and is engaged by the alignment guide 110. The prosthetic stem 126 is inserted into the cavity while maintaining contact with the alignment guide 110. A surgeon may apply lateral pressure using the handle 112 in order to ensure a sufficient engagement between the prosthetic stem 126 and the alignment guide 110 to prevent undesired rotation of the stem 126.

The alignment guide 110 may be removed from the stem 126 prior to final seating of the stem 126 within the cavity. In addition, surface features such as flutes 132 may be longitudinally extended in a proximal direction in the area where the guide 110 meets the stem 126 in order to provide a greater duration of contact between the stem 126 and guide 110.

Although the alignment guide of the present invention is described with respect to a particular embodiment, i.e., in use with a fluted hip stem using the flutes of the stem as a key or reference, it will be apparent to those skilled in the art that various modifications may be made without departing from the character and scope of the invention. For example, the insertion guide may be used to assist the insertion of any stem like component having a keyed feature on the outer surface of the stem to key the insertion of the stem in a properly selected aligned position. The alignment guide may have any number of indentations or protrusions to key in the proper insertion of the stem of the implant.

What is claimed is:

1. An alignable orthopedic prosthesis system for implantation into a prepared bone cavity comprising:
   (a) a prosthesis including a proximal portion and a stem extending distally from the proximal portion, the stem having an outer surface including a length and at least one keyed component extending longitudinally substantially along the length of the outer surface of the stem, the proximal portion comprising a proximal geometry shaped to conform to a proximal portion of the prepared bone cavity; and
   (b) an alignment guide configured to, after insertion of at least a portion of the prosthesis into the prepared bone cavity, be removed from the prepared bone cavity while the prosthesis remains within the prepared bone cavity, the alignment guide including:
      an alignment body having an outer shape conforming to the proximal portion of the prepared bone cavity; and
      a guide surface disposed on an inner portion of the alignment body and having a key element formed therein for engageably receiving the keyed component of the prosthesis.

2. The prosthesis system of claim 1, wherein the prosthesis comprises a stem of a prosthetic joint.

3. The prosthesis system of claim 2, wherein the key element comprises at least one groove.

4. The prosthesis system of claim 2, wherein the key element comprises at least one protrusion.

5. The prosthesis system of claim 3, wherein the keyed component comprises at least one flute extending longitudinally on the stem.

6. A prosthetic stem system for implantation in a prepared cavity of a bone comprising:
   (a) a prosthetic stem including a longitudinal axis, an outer surface, and at least one stem surface feature extending along the outer surface in a substantially longitudinal direction; and
   (b) an alignment guide configured to, after insertion of at least a portion of the prosthesis into the prepared bone cavity, be removed from the prepared bone cavity while the prosthesis remains within the prepared bone cavity, the alignment guide including:
      a handle having proximal and distal ends; and
      an alignment body disposed on the distal end of the handle and having a guide surface that extends in a substantially longitudinal direction and is releasably engageable with the outer surface of the prosthetic stem and further having an outer surface that corresponds to at least a portion of the prepared bone cavity;
   wherein the guide surface includes at least one surface feature that is angled with respect to the guide surface so as to engage the stem surface feature to provide rotational stability to the prosthetic stem.

7. The stem system of claim 6, wherein the stem is fluted.

8. The stem system of claim 6, wherein the angled guide surface feature extends longitudinally along the guide surface.

9. A prosthetic stem system for implantation in a prepared cavity of a bone comprising:
   (a) a prosthetic stem including a longitudinal axis, an outer surface, and at least one stem surface feature extending along the outer surface in a substantially longitudinal direction; and
   (b) an alignment guide being laterally disengageable from the stem including:
      a handle having proximal and distal ends; and
      an alignment body disposed on the distal end of the handle and having a guide surface that extends in a substantially longitudinal direction and is releasably engageable with the outer surface of the prosthetic stem and further having an outer surface that corresponds to at least a portion of the prepared bone cavity;
   wherein the guide surface includes at least one surface feature that is angled with respect to the guide surface so as to engage the stem surface feature to provide rotational stability to the prosthetic stem.

10. The stem system of claim 6, wherein the stem is elongate, substantially cylindrical and implantatable within a prepared bone cavity of a long bone.

11. The stem system of claim 10, wherein the stem forms at least part of a femoral component for a hip prosthesis.

12. The stem system of claim 11, wherein the stem includes a proximal spout.

13. A prosthetic stem system for implantation in a prepared cavity of a bone comprising:
   (a) an elongate, substantially cylindrical prosthetic stem including a distal slot, a longitudinal axis, an outer surface, and at least one stem surface feature extending along the outer surface in a substantially longitudinal direction, the stem being implantable within a prepared cavity in a long bone; and
   (b) an alignment guide including:
      a handle having proximal and distal ends; and
      an alignment body disposed on the distal end of the handle and having a guide surface that extends in a substantially longitudinal direction and is releasably engageable with the outer surface of the prosthetic stem and further having an outer surface that corresponds to at least a portion of the prepared bone cavity;
   wherein the guide surface includes at least one surface feature that is angled with respect to the guide surface so as to engage the stem surface feature to provide rotational stability to the prosthetic stem.

14. A method for inserting a prosthetic stem into a long bone comprising the steps of:

(a) preparing a cavity in the long bone;

(b) providing a prosthetic stem having a longitudinal axis, an outer surface, and at least one stem surface feature extending along the outer surface in a substantially longitudinal direction;

(c) providing an alignment guide including an alignment body having a guide surface that extends in a substantially longitudinal direction and is releasably engageable with the outer surface of the prosthetic stem wherein the guide surface includes at least one surface feature that is angled with respect to the guide surface so as to engage the stem surface feature to provide rotational stability to the prosthetic stem, the alignment guide further having an outer shape corresponding to at least a portion of the bone cavity;

(d) placing the prosthetic stem at the opening of the cavity in the long bone in a predetermined rotational orientation;

(e) engaging the alignment guide to the prosthetic stem and to the bone cavity;

(f) inserting the prosthetic stem into the cavity while maintaining sliding contact with the alignment guide; and (g) removing the alignment guide from the prosthetic stem.

* * * * *